United States Patent
De Rosa et al.

(10) Patent No.: US 8,592,186 B2
(45) Date of Patent: Nov. 26, 2013

(54) BIOTECHNOLOGICAL PRODUCTION OF CHONDROITIN

(75) Inventors: Mario De Rosa, Naples (IT); Chiara Schiraldi, Naples (IT); Donatella Cimini, Naples (IT)

(73) Assignee: Altergon S.A., Lugano (CH)

( * ) Notice: Subject to any disclaimer, the term of this patent is extended or adjusted under 35 U.S.C. 154(b) by 0 days.

(21) Appl. No.: 13/322,185

(22) PCT Filed: May 25, 2010

(86) PCT No.: PCT/EP2010/057129
§ 371 (c)(1),
(2), (4) Date: Nov. 23, 2011

(87) PCT Pub. No.: WO2010/136435
PCT Pub. Date: Dec. 2, 2010

(65) Prior Publication Data
US 2012/0135470 A1    May 31, 2012

(30) Foreign Application Priority Data
May 25, 2009  (IT) .............................. MI2009A0923

(51) Int. Cl.
*C12P 19/04*    (2006.01)

(52) U.S. Cl.
USPC ...................................................... 435/101

(58) Field of Classification Search
None
See application file for complete search history.

(56) References Cited

U.S. PATENT DOCUMENTS

| | | |
|---|---|---|
| 6,777,398 B2 | 8/2004 | Zoppetti et al. |
| 2003/0162267 A1 * | 8/2003 | Pompejus et al. ............ 435/106 |

FOREIGN PATENT DOCUMENTS

| | | |
|---|---|---|
| WO | 01/02597 A | 1/2001 |
| WO | 01/80810 A | 11/2001 |
| WO | WO 2006/023546 A2 * | 3/2006 |
| WO | WO 2009/098246 A1 * | 8/2009 |

OTHER PUBLICATIONS

Verpoorte et al., Curr. Opinion Biotechnol. 13:181-187, 2002.*
Rode et al., J. Biotechnol. 135:202-209, 2008.*
Cimini et al., Appl. Microbiol. Biotechnol. 85:1779-1787, Oct. 2009.*
Schiraldi et al., Biotechnol. Bioengineer. 70:670-676, 2000.*
Schiraldi et al., Extremophiles 3:199-204, 1999.*
Bailey, Marc J. A. et al., "Increased distal gene transcription by the elongation factor RfaH, a specialized homologue of NusG" Molecular Microbiology, Wiley-Blackwell Publishing Ltd, GB, vol. 22, No. 4, Jan. 1, 1996, pp. 729-737, XP009097121, ISSN: 0950-382X.
Bailey, Marc J. A. et al., "*Escherichia coli* Hlyt Protein, A Transcriptional Activator of Haemolysin Synthesis and Secretion, is Encoded by the RFAH (SFRB) Locus Required for Expression of Sex Facotr and Lipopolysaccharide Genes" Molecular Microbiology, Wiley-Blackwell Publishing Ltd, GB, vol. 6, No. 8, Jan. 1, 1992, pp. 1003-1012, XP000891242, ISSN: 0950-382X.
Rahn, Andrea et al., "Transcriptional organization and regulation of the *Escherichia coli* K30 group 1 capsule biosynthesis (cps) gene cluster." Molicular Micorbiology, vol. 47, No. 4, Feb. 2003, pp. 1045-1060, XP002569165, ISSN: 0950-382X.
Carter, Heather D. et al., "Highly divergent RfaH orthologs from pathogenic proteobacteria can substitute for *Escherichia coli* RfaH both in vivo and in vitro" Journal of Bacteriology, vol. 186. No. 9, May 2004, pp. 2829-2840, XP002569166, ISSN: 0021-9193.
Manzoni, M. et al., "Production and purification of an extracellularly produced K4 polysaccharide from *Escherichia coli*" Biotechnology Letters, vol. 18, No. 4, 1996, pp. 383-386, XP002569167, ISSN: 0141-5492.
Stevens, Mark P. et al., "Regulation of the *Escherichia coli* K5 capsule gene cluster by transcription antitermination" Molecular Microbiology, vol. 24, No. 5, 1997, pp. 1001-1012, XP002569168, ISSN: 0950-382X.
Taylor, C.M. et al., "Handbook of Carbohydrate Chemistry" 2005, Taylor and Francis Group, LLC, XP00256169.
International Search Report dated Apr. 11, 2011, issued in PCT/EP2010/057129.

* cited by examiner

*Primary Examiner* — David J Steadman
(74) *Attorney, Agent, or Firm* — Lucas & Mercanti, LLP

(57) ABSTRACT

An innovative method is described for the production of chondroitin at high concentration, by fermentation of genetically mutated bacteria.

11 Claims, No Drawings

SEQUENCE LISTING

```
<160> NUMBER OF SEQ ID NOS: 20

<210> SEQ ID NO 1
<211> LENGTH: 72
<212> TYPE: DNA
<213> ORGANISM: Escherichia coli
<220> FEATURE:
<221> NAME/KEY: primer_bind
<222> LOCATION: (1)..(72)

<400> SEQUENCE: 1
cagcacagca gagcgaagtg carcatatcc ttccagattt aaattcttca aattaaccct      60
cactaaaggg cg                                                         72

<210> SEQ ID NO 2
<211> LENGTH: 22
<212> TYPE: DNA
<213> ORGANISM: Escherichia coli
<220> FEATURE:
<221> NAME/KEY: primer_bind
<222> LOCATION: (1)..(22)

<400> SEQUENCE: 2
taatacgact cactataggg ct                                              22

<210> SEQ ID NO 3
<211> LENGTH: 23
<212> TYPE: DNA
<213> ORGANISM: Escherichia coli
<220> FEATURE:
<221> NAME/KEY: primer_bind
<222> LOCATION: (1)..(23)

<400> SEQUENCE: 3
taatacgact cactataggg ctc                                             23

<210> SEQ ID NO 4
<211> LENGTH: 33
<212> TYPE: DNA
<213> ORGANISM: Escherichia coli
<220> FEATURE:
<221> NAME/KEY: primer_bind
<222> LOCATION: (1)..(33)

<400> SEQUENCE: 4
cgggatcccg atattccacc agctatttgt tag                                  33

<210> SEQ ID NO 5
<211> LENGTH: 34
<212> TYPE: DNA
<213> ORGANISM: Escherichia coli
<220> FEATURE:
<221> NAME/KEY: primer_bind
<222> LOCATION: (1)..(34)

<400> SEQUENCE: 5
cgggatcccg atgcaatcct ggattttact gtac                                 34
```

```
<210> SEQ ID NO 6
<211> LENGTH: 73
<212> TYPE: DNA
<213> ORGANISM: Escherichia coli
<220> FEATURE:
<221> NAME/KEY: primer_bind
<222> LOCATION: (1)..(73)

<400> SEQUENCE: 6
aaactgtgat cgggcgtagg aacccgcgta gtcatcgtcg gcgcagaagt ttagagtttg      60
cggaactcgg tat                                                        73

<210> SEQ ID NO 7
<211> LENGTH: 23
<212> TYPE: DNA
<213> ORGANISM: Escherichia coli
<220> FEATURE:
<221> NAME/KEY: primer_bind
<222> LOCATION: (1)..(23)

<400> SEQUENCE: 7
gccattaaga aatacacgat tcc                                             23

<210> SEQ ID NO 8
<211> LENGTH: 23
<212> TYPE: DNA
<213> ORGANISM: Escherichia coli
<220> FEATURE:
<221> NAME/KEY: primer_bind
<222> LOCATION: (1)..(23)

<400> SEQUENCE: 8
atctttattc tcatggctga acg                                             23

<210> SEQ ID NO 9
<211> LENGTH: 809
<212> TYPE: DNA
<213> ORGANISM: Escherichia coli
<220> FEATURE:
<221> NAME/KEY: primer_bind
<222> LOCATION: (1)..(809)

<400> SEQUENCE: 9
cagcacagca gagcgaagtg carcatatcc ttccagattt aaattcttca aaattaaccc      60
tcactaaagg gcggccgcga agttcctatt ctctagaaag tataggaact tcctcgaggg     120
cctttaaaat tcggggcgcc gaccccatgt ggtctcaagc ccaaaggaag agtgaggcga     180
gtcagtcgcg taatgcttag gcacaggatt gatttgtcgc aatgattgac acgattccgc     240
ttgacgctgc gtaaggtttt tgtaatttta caggcaacct tttattcact aacaaatagc     300
tggtggaata tcgggatccc gatgcaatcc tggtatttac tgtactgcaa gcgcgggcaa     360
cttcaacgtg cccaggaaca cctcgaaaga caggctgtga attgcctggc accgatgatc     420
accctggaaa aaatcgtgcg tggaaaacgt actgcagtca gtgagccatt gtttcccaac     480
tacctgtttg tcgaatttga tccagaagtg attcatacca cgactatcaa cgcgacccgc     540
ggtgtcagtc acttcgtgcg ctttggcgcg tcgccagcga tagtcccatc ggcggtgatt     600
catcagctat cggtatataa accgaaagac attgtcgatc cggcaacccc ttatccggga     660
gataaggtga ttattaccga aggcgcgttc gaaggctttc aggccatttt caccgaaccc     720
gatggtgagg ctcgctccat gctattgctt aatcttatta ataaagagat taagcacagt     780
gtgaagaata ccgagttccg caaactcta                                       809
```

```
<210> SEQ ID NO 10
<211> LENGTH: 30
<212> TYPE: DNA
<213> ORGANISM: Escherichia coli
<220> FEATURE:
<221> NAME/KEY: primer_bind
<222> LOCATION: (1)..(30)

<400> SEQUENCE: 10
gcctcgaggc gatcaaacag tgatatacgc                                         30

<210> SEQ ID NO 11
<211> LENGTH: 123
<212> TYPE: DNA
<213> ORGANISM: Escherichia coli
<220> FEATURE:
<221> NAME/KEY: primer_bind
<222> LOCATION: (1)..(123)

<400> SEQUENCE: 11
caccctggcg cccaatacgc aaaccgcctc tccccgcgcg ttggccgatt cattaatgca        60
gctggcacga caggtttccc gactggaaag cgggcagtga aattaaccct cactaaaggg       120
cgg                                                                    123

<210> SEQ ID NO 12
<211> LENGTH: 123
<212> TYPE: DNA
<213> ORGANISM: Escherichia coli
<220> FEATURE:
<221> NAME/KEY: primer_bind
<222> LOCATION: (1)..(123)

<400> SEQUENCE: 12
aaaagaataa accgaacatc caaaagtttg tgttttttaa atagtacata atggatttcc        60
ttacgcgaaa tacgggcaga catggcctgc ccggttattt agagtttgcg gaactcggta       120
ttc                                                                    123

<210> SEQ ID NO 13
<211> LENGTH: 958
<212> TYPE: DNA
<213> ORGANISM: Escherichia coli
<220> FEATURE:
<221> NAME/KEY: primer_bind
<222> LOCATION: (1)..(958)

<400> SEQUENCE: 13
caccctggcg cccaatacgc aaaccgcctc tccccgcgcg ttggccgatt cattaatgca        60
gctggcacga caggtttccc gactggaaag cgggcagtga aattaaccct cactaaaggg       120
cggccgcgaa gttcctattc tctagaaagt ataggaactt cctcgagggc ctttaaaatt       180
cggggcgccg accccatgtg gtctcaagcc caaaggaaga gtgaggcgag tcagtcgcgt       240
aatgcttagg cacaggattg atttgtcgca atgattgaca cgattccgct tgacgctgcg       300
taaggttttt gtaatttttac aggcaacctt ttattcacta acaaatagct ggtggaatat       360
cgggatcccg atgcaatcct ggtatttact gtactgcaag cgcgggcaac ttcaacgtgc       420
ccaggaacac ctcgaaagac aggctgtgaa ttgcctggca ccgatgatca ccctggaaaa       480
aatcgtgcgt ggaaaacgta ctgcagtcag tgagccattg tttcccaact acctgtttgt       540
cgaatttgat ccagaagtga ttcataccac gactatcaac gcgacccgcg gtgtcagtca       600
cttcgtgcgc tttggcgcgt cgccagcgat agtcccatcg gcggtgattc atcagctatc       660
ggtatataaa ccgaaagaca ttgtcgatcc ggcaaccct tatccgggag ataaggtgat       720
```

-continued

```
tattaccgaa ggcgcgttcg aaggctttca ggccattttc accgaacccg atggtgaggc    780
tcgctccatg ctattgctta atcttattaa taaagagatt aagcacagtg tgaagaatac    840
cgagttccgc aaactctata ataaccgggc aggccatgtc tgcccgtatt tcgcgtaagg    900
aaatccatta tgtactattt aaaaaacaca aactttggga tgttcggttt attctttt     958
```

```
<210> SEQ ID NO 14
<211> LENGTH: 31
<212> TYPE: DNA
<213> ORGANISM: Escherichia coli
<220> FEATURE:
<221> NAME/KEY: primer_bind
<222> LOCATION: (1)..(31)

<400> SEQUENCE: 14
cgggatccga atgcaatcct ggtatttact g                                    31

<210> SEQ ID NO 15
<211> LENGTH: 29
<212> TYPE: DNA
<213> ORGANISM: Escherichia coli
<220> FEATURE:
<221> NAME/KEY: primer_bind
<222> LOCATION: (1)..(29)

<400> SEQUENCE: 15
cggagctctt agagtttgcg gaactcggt                                       29

<210> SEQ ID NO 16
<211> LENGTH: 45
<212> TYPE: DNA
<213> ORGANISM: Escherichia coli
<220> FEATURE:
<221> NAME/KEY: primer_bind
<222> LOCATION: (1)..(45)

<400> SEQUENCE: 16
tggatttgcc cctatgtttc cagatacctg ttatcactta aagct                     45

<210> SEQ ID NO 17
<211> LENGTH: 41
<212> TYPE: DNA
<213> ORGANISM: Escherichia coli
<220> FEATURE:
<221> NAME/KEY: primer_bind
<222> LOCATION: (1)..(41)

<400> SEQUENCE: 17
ttaagtgata acaggtatct ggaaacatag ggcaaatcc a                          41

<210> SEQ ID NO 18
<211> LENGTH: 22
<212> TYPE: DNA
<213> ORGANISM: Escherichia coli
<220> FEATURE:
<221> NAME/KEY: primer_bind
<222> LOCATION: (1)..(22)

<400> SEQUENCE: 18
tagactggcc ccctgaatct cc                                              22
```

```
<210> SEQ ID NO 19
<211> LENGTH: 32
<212> TYPE: DNA
<213> ORGANISM: Escherichia coli
<220> FEATURE:
<221> NAME/KEY: primer_bind
<222> LOCATION: (1)..(32)

<400> SEQUENCE: 19
cgggatcctc caatgactag tctaaaaact ag                                    32

<210> SEQ ID NO 20
<211> LENGTH: 629
<212> TYPE: DNA
<213> ORGANISM: Escherichia coli
<220> FEATURE:
<221> NAME/KEY: primer_bind
<222> LOCATION: (1)..(629)

<400> SEQUENCE: 20
tagactggcc ccctgaatct ccagacaacc aatatcactt aaataagtga tagtcttaat      60
actagttttt agactagtca ttggaggatc cgaatgcaat cctggtattt actgtactgc     120
aagcgcgggc aacttcaacg tgcccaggaa cacctcgaaa gacaggctgt gaattgcctg     180
gcaccgatga tcaccctgga aaaaatcgtg cgtggaaaac gtactgcagt cagtgagcca     240
ttgtttccca actacctgtt tgtcgaattt gatccagaag tgattcatac cacgactatc     300
aacgcgaccc gcggtgtcag tcacttcgtg cgctttggcg cgtcgccagc gatagtccca     360
tcggcggtga ttcatcagct atcggtatat aaaccgaaag acattgtcga tccggcaacc     420
ccttatccgg gagataaggt gattattacc gaaggcgcgt tcgaaggctt tcaggccatt     480
ttcaccgaac ccgatggtga ggctcgctcc atgctattgc ttaatcttat taataaagag     540
attaagcaca gtgtgaagaa taccgagttc cgcaaactct aagagctctt aagtgataac     600
aggtatctgg aaacataggg gcaaatcca                                       629
```

BIOTECHNOLOGICAL PRODUCTION OF CHONDROITIN

This application is a U.S. national stage of PCT/EP2010/057129 filed on May 25, 2010 which claims priority to and the benefit of Italian Application No. MI2009A000923 filed on May 25, 2009, the contents of which are incorporated herein by reference.

STATE OF THE ART

Chondroitin is a natural linear polysaccharide formed by alternating residues of N-acetyl-D-galactosamine β 1:4 and D-glucuronate β 1:3. In vertebrates, chondroitin is present in various sulphated forms originated by sulfation of hydroxyl residues 4 and 6 of N-acetyl-D-galactosamine and, in some cases, of residues 2 and 3 of glucuronic acid (Sugahara K et al., J. Biol. Chem., 1996, 271, 26745-54). The molecular weight of chondroitin and the extent and sites of sulfation depend on the type and age of tissues (Kuettner K E et al., Eds., in Articular cartilage and osteoarthritis, NY, Raven Press, 1992; Volpi N Ed., in Chondroitin sulfate: structure, role and pharmacological activity, S. Diego, Calif. Academic Press-Elsevier Inc, 2006). Chondroitin sulfate belongs to the wider family of glycosaminoglycans, termed GAGs (Beaty N B, and Mello R J, J. Chromatography and Biomedical Applications, 1987, 418, 187-222). These polysaccharides, covalently linked to proteins, as proteoglycans are ubiquitous components of the extracellular matrix of all connective tissues, which perform many functions. (Ruoslathi E, Ann. Rev. Cell. Biol., 1988, 4, 229-255; Kjellen L and Lindahl U, Ann. Rev. Biochem., 1991, 60, 443-76).

Some pathogenic bacteria produce a capsular structure that serves as a virulence factor. In some cases the capsule is formed by GAG or related structures in order to trick the immune system during infection. Examples of these pathogens are *Pasteurella multocida* (DeAngelis P L, et al., Carbohydrate Res. 2002, 337(17), 1547-52; Harper M, et al., FEMS Microbiol. Lett., 2006, 265(1), 1-10; Leonov A V, et al., Zh. Mikrobiol. Epidemiol. Immunobiol. 2006, November-December (7), 94-7), encapsulated strains K4 and K5 *E. coli* (Roberts I S, Ann. Rev. Microbiol. 1996, 50, 285-31; Bronner D, et al., J Bacteriol. 1993 September; 175(18): 5984-92; Jann B and Jann K In *Escherichia coli*: Mechanisms of virulence. Cambridge Univ. Press. 1997; Whitfield C, Annu. Rev. Biochem. 2006, 75:39-68. Stevens M P, et al., Mol. Microbiol. 1997, 24(5), 1001-12; Whitfield C and Roberts I S, Mol. Microbiol. 1999, 31, 1307-20; Ninomiya T, et al., J. Biol. Chem. 2002, 277(24), 21567-75) and some strains of capsulated streptococci (Wessels M R, et al., Proc. Nat. Acad. Sci. USA, 1991, 88, 19, 8317-21; Tlapak-Simmons V L et al., J. Biol. Chem., 2005, 280, 13, 13012-18).

Chondroitin sulfate is used as anti-rheumatic and chondro-protective drug, with applications in the treatment of tibiofibular osteoarthritis of the knee and osteoarthritis of the articular cartilage (Kuettner K E et al., Eds., in Articular cartilage and osteoarthritis, NY, Raven Press, 1992; Simànek V et al., 2005, 149, 51-56; Goerres G W et al., J. Clinical Desitometry 2005, 8, 484-487; Altman R D et al., OsteoArthritis and Cartilage 2005, 13, 13-19; Chan P S, et al., OsteoArthritis and Cartilage 2005, 13, 387-394; Chou M M, et al., Exp. Biol. Med. 2005, 230, 255-262; Clegg D O, et al., New England J. of Medicine, 2006, 23, 795-808; Roman-Blas et al., OsteoArthritis and Cartilage, 2006, 14, 839-848; Maheu E et al., OsteoArthritis and Cartilage, 2006, 14, 303-322; Fotinì N et al., Biomed. Chromatogr. 2006, 20, 539-550; Lagnaoui R et al., Thérapie 2006, 61, 341-346; Volpi N Ed. in Chondroitin sulfate: structure, role and pharmacological activity, S. Diego, Calif. Academic Press-Elsevier Inc, 2006; Zhang W et al., Ann. Rheum. Dis. 2007, 66, 377-388). Currently, chondroitin sulfate is obtained by extraction techniques from various animal sources, such as pig cartilage, shark fin and cartilage from teleosts. The shortage of raw material and the complexity of the downstream purification process limit worldwide the availability of this active ingredient, therefore the market is controlled by the impossibility to satisfy a growing demand. Moreover, in perspective, the chondroitin sulfate obtained by extraction may be excluded from the pharmaceutical market due to increasingly stringent regulations on the safety of animal-derived drugs, that are continuously enacted.

Therefore, there is a growing interest in developing alternative biotechnological strategies for production of this type of polysaccharides, or their precursors, by fermentation of suitable microorganisms.

Reports in the scientific literature (Rodriguez M L et al., Eur. J. Biochem., 1988, 177, 117-24; Manzoni M et al., Biotechnology Letters, 1996, 18, 383-6) and patent literature (WO 01/02597 A1) showed the possibility to obtain chondroitin by fermentation, using a *E. coli* K4 strain producing a chondroitin derivative, the K4 polysaccharide, whose carbon backbone is identical to chondroitin, except for the addition of β-fructofuranose residues at the level of C3 of glucuronic acid. Chondroitin can be obtained from the K4 polysaccharide by controlled acid hydrolysis of fructose residues (U.S. Pat. No. 6,288,044; U.S. Pat. No. 6,777,398). However, production of chondroitin from the K4 precursor did not develop as a real industrial process due to the low yields of polysaccharide precursor during fermentation, in the best case not exceeding $0.42 \, g \cdot L^{-1}$ (WO01/02597).

The U.S. 2005266460 and a series of previously reported patent documents (WO 0180810, EP 1282684, EP 1832662, U.S. 20030104601, U.S. 20050164984) describe the use of chondroitin synthase from *Pasteurella multocida*, an enzyme that catalyzes the synthesis of chondroitin from the corresponding UDP sugars. In particular, these documents claim the segment of nucleotide sequence coding for the enzyme, the construction and use of recombinant systems (expression systems in prokaryotes and eukaryotes) which express such segment of nucleotide sequence and the production from such recombinant systems of chondroitin of various sizes. All documents lack the experimental data about the processes claimed, in particular the data about mode of fermentation to produce enzymes and yields of chondroitin in the biotechnological process are never reported in detail. About 10 years after the first priority, no industrial process has been developed that relates to what was claimed.

U.S. 20070015249 and the previously reported patent document U.S. 20030109693 describe the production of a chondroitin synthase from *E. coli* K4 and its use for in vitro production of chondroitin. Production of the enzyme, encoded by the kfoC gene of *E. coli* K4, located in region II of the gene cluster responsible for the biosynthesis of the capsular antigen, is characterized by the following steps: kfoC amplification, cloning of the gene in vector pTrcHis and expression from the commercial *E. coli* TOP strain. The two documents also claim proteins with natural or artificial mutations which may cause slight structural changes of chondroitin synthase without altering its catalytic function. Also these documents lack data regarding the yields of the claimed manufacturing processes, the production of chondroitin synthase and in vitro production of chondroitin from the corresponding UDP-sugars.

EP 1950308 and a series of previous patent documents (WO 2007145197, WO 2007069693, WO 2007058252, WO 2007058252, WO 2007023867) describe methods for in vitro synthesis of chondroitin and its derivatives using chondroitin synthase from *E. coli* K4 and its mutants, which have only one of the two transferase activities.

U.S. Pat. No. 7,273,729 and a series of previous patent documents (JP 2004024208, US 20060052335, US 20060057697, U.S. Pat. No. 7,232,676) describe the use of human chondroitin synthase, an enzyme that catalyzes the synthesis of chondroitin from the corresponding UDP sugars. The documents claim the structure of human chondroitin synthase, an expression vector comprising the sequence of the enzyme, the expression of said vector in eukaryotic cells and a method to synthesize the polysaccharide chain of chondroitin.

U.S. 20070059805 claims the structure of human chondroitin synthase, an expression vector comprising the sequence of the enzyme, the expression of said vector in eukaryotic cells and a method to synthesize the polysaccharide chain of chondroitin.

All the above mentioned documents do not solve the problem of chondroitin production at competitive costs compared to chondroitin sulfate obtained by extraction from animal sources. In particular, production by fermentation using *E. coli* K4, *Pasteurella multocida* and their chondroitin synthase mutants, is characterized by yields not exceeding 0.5 g·L$^{-1}$ in the fermentation broth. Similarly biotechnological processes using chondroitin synthase from *E.* K4 *coli*, *Pasteurella multocida* or from human and their mutants have high costs associated with enzyme production and the use of UDP sugars as substrates.

Thus the problem of producing chondroitin at costs compatible with the needs of the market remains without practical solutions.

SUMMARY OF THE INVENTION

Surprisingly it was found that chondroitin can be produced by fermentation obtaining yields >8 gL$^{-1}$ by use of an integrated strategy based on optimization of a three-phase fermentation process (batch-fed batch-in microfiltration regimen) and genetically modified bacteria. Said bacteria are preferably genetically modified strains of *E. coli* K4, whereby the aim of the engineering process is to improve processivity of the whole enzyme complex responsible for the synthesis of the K4 polysaccharide, by inserting multiple copies of the autologous RfaH gene, which acts as positive regulator of transcription of the gene cluster responsible for the synthesis of capsular material.

High yields, ease of the downstream purification process developed, low total cost of the process and low environmental impact make these findings superior to the previously described biotechnological strategies (Rodriguez M L et al., Eur. J. Biochem., 1988, 177, 117-124; Manzoni M et al., Biotechnology Letters, 1996, 18, 383-386; WO 01/02597 A1; U.S. Pat. No. 6,288,044; U.S. Pat. No. 6,777,398; US 2005266460; WO 01/80810; EP 1282684; EP 1832662; US 20030104601; US 20050164984; US 20070015249; US 20030109693; EP 1950308; WO 2007145197; WO 2007069693; WO 2007058252; WO 2007058252; WO 2007023867; U.S. Pat. No. 7,273,729; JP 2004024208; US 20060052335; US 20060057697; U.S. Pat. No. 7,232,676; US 20070059805).

The fermentation process developed, integrated with a strategy of site-selective chemical sulphation of chondroitin makes the claimed biotechnological process competitive compared to the conventional processes of extraction of chondroitin sulfate from raw materials of animal origin, which may be removed from the pharmaceutical market due to recent changes of regulations about product safety.

DETAILED DESCRIPTION OF THE INVENTION

The present invention describes a fermentation process which, by use of genetically modified bacterial microorganisms such as *E. coli*, preferably K4, and by use of special growth conditions allows production of capsular polysaccharides, chondroitin precursors (chondroitin fructosylated on glucuronic acid in position 3, in the case of polysaccharide K4) and to obtain yields higher than 8 g·L$^{-1}$, that is about 20-fold more than hitherto described.

This strategy is characterized by the following phases:

a multi-step fermentation process (batch, fed-batch, in micro-filtration regimen), employing a recombinant strain of *E. coli* K4 characterized by the presence of multiple copies of the autologous RfaH gene (Santangelo and Roberts T. J Mol Cell 2002 Apr. 9 (4):698-700) which is a positive regulator of transcription of the gene cluster responsible for the synthesis of capsular material; hydrolytic treatment made directly on the depleted fermentation broth devoid of the biomass, which enables the conversion of polysaccharide K4 to chondroitin and fructose and the simultaneous detoxification of the fermentation supernatant by cleavage of lipopolysaccharide (LPS), produced in high amounts by the microorganism, in O-chain and lipid A, which immediately precipitates, allowing its easy removal; an innovative downstream purification processes based on membrane processes capable of separating the chondroitin O-chain from other contaminants present in the culture medium.

The process claimed is inventive and innovative compared to the prior art, because it is the only one that allows implementation of processes on an industrial scale for production of chondroitin, a polysaccharide of great potential for the pharmaceutical market, for which no production, extraction or biotechnological processes have been achieved up to now. Furthermore, the process claimed, integrated with a strategy of site-selective sulfation of chondroitin, now makes possible to meet the growing demand of chondroitin sulfate that comes from the market, bypassing the problems of current production strategies based on extraction and associated with the use of animal sources.

Engineering of Bacterial Strains

Wild type *E. coli* K4 (EcK4wt)—There are many known strains of *E. coli*, all encapsulated, categorized in four different serological groups based on the capsular antigenic determinants (about 80 antigenic determinants are known to date) and on physical, biochemical and genetic criteria. Capsules of group 1 and 4 belong to strains of *E. coli* responsible for intestinal infections including enteropathogenic (EPEC), enterotoxigenic (ETEC) and enterohemorrhagic (EHEC) strains. Group 1 capsules are formed by polysaccharides which are acidic due to the presence of uronic acids with quite similar structures. Group 4 capsular structures are instead very different and are characterized by the presence of Nacetylated amino sugars in their repeating units. Capsules in groups 2 and 3 belong to strains of *E. coli* responsible for extraintestinal infections (ExPEC). EcK4wt, the microorganism subjected to genetic modification for over-production of the K4 polysaccharide, belongs to serological group 2 and is available with different codes in the major banks of microorganisms such as American Type Culture Collection, USA (ATCC 23502), International *Escherichia* Centre, Denmark (strain Bi 8337/41), National Collection of Type Cultures, UK (strain NCTC 9005) and Freiburg collection (strain U1-41 2616).

Surprisingly it was found that EcK4wt carries an endogenous plasmid, henceforth identified with the acronym PK4, whose presence in *E. coli* K4 is not described in the literature.

pK4 consists of about 93,000 bases, is constitutive and is characterized in that it comprises sequences that can be used to insert the heterologous gene sequences ID NO:1 e/o ID NO:6. On average it is present in 1-5 copies/cell and its genetic modifications are stable.

RfaH, the transcriptional regulator of the gene cluster responsible for the synthesis of capsular material—The transcription of long polycistronic operons in bacteria is often based on accessory proteins, whose molecular mechanisms remain unknown. For example, transcription of a single mRNA molecule from regions 2 and 3 of the gene cluster responsible for the synthesis of molecular components of the capsule is controlled by a protein encoded by the antiterminator gene rfaH, which therefore functions as a positive regulator of transcription, preventing the premature arrest of transcripts. By increasing the processivity of RNA polymerase, the protein encoded by the RfaH gene activates transcription of several genes responsible for virulence and fertility of enteric bacteria (Stevens M P et al. Mol. Microbiological., 1997, 24, 1001-12). In general, the protein encoded by the RfaH gene is required for biosynthesis of the lipopolysaccharide core of *E. coli* and *S. typhimurium* (Pradel E and Schnaitman C A, J. Bacteriol., 1991, 173, 6428-31; Brazas R, et al., J. Bacteriol. 1991, 173, 6168-73), for the synthesis and secretion of α-hemolysin (Bailey M J A et al., Mol. Microbiol. 1992, 6, 1003-10) and for the production of sex factor-F (Beutin L and Achtman M J, Bacteriol. 1979, 139, 730-37). Moreover Zhang and coworkers (Zhang L et al. Infect. Immuno. 2004, 72, 7282-93) reported that, in general, the expression of capsular antigens of serological group 2 requires the protein encoded by the rfaH gene and showed that said protein is required for transcription of region 2 of the gene cluster responsible for the synthesis of capsular polysaccharide in *E. coli* K5. Rahn and Whitfield (Rahn A and C. Whitfield, Mol. Microbiological. 2003, 47, 1045-60) showed that, in *E. coli* K30 of serological group I, transcription of the cluster for synthesis of the capsule is modulated by an antitermination mechanism exerted by the RfaH gene.

The essential role of the RfaH gene and corresponding protein in the process of synthesis of capsular components is indirectly demonstrated by studies involving deletion or alterations of this gene. In particular, Nagy and collaborators (Nagy G, et al., Infect. Immun. 2002, 70, 4406-13) reported that deletion of the rfaH gene from the genome of uropathogenic *E. coli* 536 strain drastically reduces virulence in mice, from 100% mortality induced by the wild type strain to 18% by the mutant strain. Elimination of the RfaH gene also determines an alteration of the LPS phenotype and reduced K15 capsule and α-hemolysin production. Stevens and collaborators (Stevens M P et al., FEMS Microbiol. Lett., 1994, 124, 93-8) show that introducing mutations in the rfaH gene sequence disables capsule production at 37° C. in *E. coli* K5 cells.

In contrast, there are no available data in the literature on the effect of rfaH over-expression.

In strain EcK4wt, the rfaH gene is under control of a regulated promoter, which determines maximum expression during the stationary growth phase (Stevens M P, et al. Mol. Microbiol., 1997, 24, 1001-12; Stevens M. P., et al., FEMS Microbiol. Lett., 1994, 124, 93-98).

Surprisingly it was found that integration of one or more copies of the rfaH gene in the genetic material of bacteria such as *E. coli*, especially EcK4wt, considerably improves production of the K4 polysaccharide. To achieve more effective transcription, the integrated rfaH gene can be placed under the control of a promoter which is preferably efficient at all stages of growth, such as pGap, a constitutive promoter of the GapA gene encoding the glyceraldehyde-3-P-dehydrogenase (GAPDH) which is a key enzyme necessary for *E. coli* metabolism. In particular, the pGap promoter is organized in a multi-promoter region composed of P1, P2, P3 and P4 promoters. Of those, the P1 promoter is the strongest, however the four promoters act synergistically to ensure gene transcription in different conditions, making it more versatile and efficient. Other constitutive promoters which are active in *E. coli* can still be used.

Therefore further object of the invention is a bacterial strain having a chondroitin precursor as capsular polysaccharide, preferably an engineered *Escherichia coli* strain, in which said polysaccharide is preferably K4, characterized in that it comprises at least one copy of a sequence coding the rfaH protein or its functionally equivalent fragments.

This can be engineered by insertion of multiple gene copies as chromosomal DNA elements or as plasmid elements or transposable elements, alternatively or in combination.

According to a preferred realization, the sequence coding for the rfaH protein is placed under the control of a constitutive promoter or comprises at least one sequence selected from the group consisting of: SEQ ID NO:1 SEQ ID NO:6, SEQ ID NO:9, SEQ ID NO:11, SEQ ID NO:12, SEQ ID NO:13, SEQ ID NO:20. Surprisingly it was found that high yields of K4 polysaccharide can be obtained from these engineered bacteria by using a fermentation process carried out in three sequential steps: batch, fed-batch and microfiltration regimen.

The first batch phase lasts until a decrease in microbial (μ) growth rate occurs as result of nutrient depletion, leading to a simultaneous increase of $pO_2$.

The second fed-batch phase is critically characterized by a feeding profile that makes use of a concentrated solution of nutrients supporting microbial growth to a rate that is less than maximal. In particular, the claimed fermentation strategy involves the possibility that addition of nutrients is automatically optimized by driving the feed with variations of fermentation parameters typically correlated with conditions of nutrient availability, such as partial $O_2$ pressure or pH of the culture medium. This strategy is implemented by creating control loops with a dedicated software ensuring, based on optimized parameters of PID controllers, real-time adjustments in order to meet the nutritional requirements of microbial growth, thereby prolonging the growth phase and avoiding metabolism overflow phenomena which could lead to accumulation in the medium of organic acids inhibitory to growth (in the case of EcK4 a concentration of acetic acid>5 $g \cdot L^{-1}$ inhibits growth).

The third phase, termed microfiltration regimen, is activated when the accumulation of toxic catabolites slows down or stops growth, even in presence of available nutrients. This process involves microfiltration of the culture medium using microfiltration modules placed inside or outside the bioreactor. During microfiltration, the fermented volume is kept constant by a level controller, which automatically restores the volume of the micro-filtrate removed by addition of saline with composition compatible with that used for medium preparation. At the end of the fermentation process, the K4 polysaccharide is present partly in microfiltrate and partly in the fermentor.

Batch growth—The release of K4 polysaccharide in the culture medium is a constitutive feature of EcK4r and EcK4wt, while the biomass yield and productivity (K4 polysaccharide/biomass) depend on the composition of the culture medium and fermentation conditions.

Nutrients—For production of K4 polysaccharide, culture media with different composition can be used for growth of EcK4r and EcK4wt; for example, glucose, dextrin, starch, glycerol, corn steep liquor, molasses can be used as carbon sources and peptone, yeast extract, casein hydrolysate, tryptone and soy, cotton and pea flours can be used and as non-animal sources of organic nitrogen and complex nutrients. However, the ratio between carbon source and organic nitrogen source in the culture medium is critical for efficient production (K4 polysaccharide/biomass). In particular, decreasing the amount of organic nitrogen in the culture medium results in lower growth capacity of the microorganism, associated with a greater ability to produce the K4 polysaccharide. Since this second effect outweighs the first, a higher productivity (polysaccharide K4/L fermentation) is observed in semidefined media poor in complex sources.

Oxygenation—Oxygenation of the culture medium has no critical effects on growth of the microorganism and production of K4 polysaccharide, as long as conditions of strict anoxia are avoided, ensuring at least a $pO_2>5\%$ saturation in pure oxygen.

pH—growth occurs between pH 3 and 10, while the pH range 6-8 is optimal for growth of the microorganism and for production of K4 polysaccharide. Therefore, the pH of the culture medium is automatically maintained within this pH interval with a pH-stat system.

Temperature—growth of the microorganism and production of K4 polysaccharide occurs in the 25-40° C. interval, with maximum yield at 37° C.

Growth phase—The microorganism releases the K4 polysaccharide in the culture medium, partially in the exponential growth phase and completely in the stationary phase.

Growth in flask and fermentor—Under comparable growth conditions, the fermentor gives 4-fold higher yields (K4 polysaccharide/L of fermentation) compared to the flask.

Fed-batch growth—Surprisingly it was found that feed strategies avoiding overflow metabolism, obtained by keeping addition of fresh nutrients below the critical rate of substrate uptake, improve the yields of biomass and polysaccharide K4. For example, this can be achieved with a fermentation strategy in which the feed of nutrients is placed under control of the concentration of oxygen dissolved in the reactor, which should be maintained at a $pO_2$ of 30%. This is accomplished quickly and reproducibly by a PID controller connected to the feeding pump delivering a concentrated nutrient solution (e.g. glycerol-soy or glucose-yeast extract). In fact, addition of a carbon source to the bioreactor leads to DOT decrease (Dissolved Oxygen Tension). Thus at the end of the phase of batch fermentation, especially when the $pO_2$ value begins to increase, a feed phase of concentrated nutrient supply starts and restores $pO_2$ to the setting value, with low drift (–20% of p $O_2$set). When the $pO_2$ value reaches the set-point, the feeding pump stops automatically and shuts off feeding, until the carbon source in the fermentation broth is depleted, resulting in a sudden rise of the $pO_2$ value and triggering a new cycle as described above. The feed phase then proceeds automatically and sequentially according to the nutritional requirements of the culture under metabolic control. A similar strategy of feed driving can be activated by working on pH variations; in this case it is necessary to exclude the automatic pH-stat system for pH adjustment, feeding will be inserted via a on-switch of the adduction pump when pH increases above a predefined threshold, based on physiology of the microorganism (e.g. pH 7.8).

Growth under microfiltration regimen—It is possible to prolong the growth phase of the microorganism and the production of K4 polysaccharide by a microfiltration process removing the toxic components that accumulate in the fermentation medium. The microfiltration process is carried out with an external unit, preferably made of hollow fibers, operating under a tangential microfiltration regimen, which reduces fouling of membrane filters and maintains a high transmembrane flow. The volume of the micro-filtrate is automatically restored with saline solution with composition identical to the culture medium, using a level control. During the microfiltration process, nutrients are added in the form of concentrated solution, according to a feeding profile that is limiting for growth rate. This allows to avoid undesired metabolic overflow phenomena and the loss of nutrients in the output current (eluate) of the micro-filtered culture medium.

These conditions result in a continuous dilution of soluble components of the fermentation medium, therefore part of the chondroitin produced is found in the permeate. The permeate obtained in the third phase of the fermentation process, under microfiltration regimen, contains low levels of macromolecular contaminants (e.g. proteins, LPS, etc.) owing to the resistance of the membrane (Rm) and the cake resistance (Rc) that is formed on the membrane. Therefore, it is possible to treat such permeate directly on the ultrafiltration (UF) membrane, avoiding protease pre-treatment, which is instead required for the depleted culture broth after removal of the cellular component. Alternatively, the microfiltration permeate is added to the depleted culture broth devoid of the cellular component.

Purification of Chondroitin from the Fermentation Broth

Separation of biomass—At the end of the fermentation process, biomass removal can be achieved either by microfiltration or centrifugation or by use of earth filtration through Funda Plate filters.

Removal of biomass by microfiltration—The microfiltration process continues at the end of the fermentation process, interrupting the addition of saline. When the amount of biomass in the microfiltrate reaches the maximum value compatible with the process (300-400 g of wet biomass $L^{-1}$, corresponding to a concentration 3-5 fold the volume of fermentation broth) one volume of deionized water is added and microfiltration is continued; this washing step is repeated at least 3 times. All permeates produced during fermentation and those associated with the removal of biomass (acellular medium) are pooled and subjected to subsequent steps of the downstream process.

Alternatively, the culture broth may be collected in a sanitized container and processed on a specific automated system for cross-flow microfiltration, using cassette or preferably hollow fibers with a cutoff between 0.22 and 0.6 m. In this case the operating conditions involve a T comprised between 15° C. and 40° C., a transmembrane pressure between 0.8 and 1.2 atm and a capacity for recirculation of tangential flow of 40-100 $L \cdot (min \cdot m^2)^{-1}$. Imposing a higher $\Delta p$ ($\geq 0.5$ atm) results in an increase of transmembrane flow and shorter treatment times, but causes formation of a thicker cake which prevents full recovery of the K4 polysaccharide in the eluate.

Removal of biomass by centrifugation—At the end of fermentation the biomass is separated from the culture broth by continuous centrifugation. If not previously ultrafiltered, the recovered culture broth is added to the microfiltration permeate prior to performing the subsequent phases of the downstream process.

Removal of Biomass by Earth Filtration

For each liter of broth, an amount of earth filter (preferably Celite) is added that is equal to 4-8 fold the weight of wet biomass in the broth, the suspension is then fed into a FUNDA type plate filter, and filtered under pressure (3-6 bar). The clarified broth (OD600≤0.1) can be treated for protein degradation possibly after microfiltration through special asymmetric microfiltration capsules (e.g. GE from 0.6 to 0.2 m).

Hydrolytic degradation of proteins—For deproteinization of the culture medium containing the K4 polysaccharide, one or more proteolytic enzymes are added, preferably fungal proteases (*Aspergillus oryzae* 2-6 UL$^{-1}$) and allowed to act for a time length dependent on the temperature used (1-3 h at 25-37° C., 8-20 h at 4° C.).

Ultrafiltration-diafiltration—The fermented material, devoid of the cellular component and deproteinized, is ultrafiltrated by use of manual or automatic systems for tangential ultrafiltration (UF) equipped with membranes assembled as cassette or hollow fiber modules, made of material compatible with the process, preferably polyethersulfone or polypropylene, with a cut-off of 50-300 KDa, preferably 100 KDa and with an area comprised between 0.02 and 0.05 m$^2$ per liter to be treated. Examples of operating ranges of UF process parameters are: capacity for tangential flow recirculation 4-10 L·min$^{-1}$; trans-membrane pressure 0.5-1.4 atm; temperature 20-40° C.; pH 4-8. The culture broth devoid of cells and deproteinized, possibly supplemented with the permeate from the fermentation phase, if it was not treated separately, is concentrated up to 10-20 fold the initial volume to remove low molecular weight contaminants (salts, peptides, residual nutrients). Subsequently, the concentrate is diafiltrated with deionized or ultrapure water (HPW 2-5 volumes) to complete the removal of low molecular weight components.

Acid treatment—The concentrate is subjected to acid hydrolysis with the dual purpose of defructosylating the K4 polysaccharide, forming chondroitin and fructose, and detoxifying the LPS lipopolysaccharide, separating the polysaccharide component (O-chain) from the lipid component (A lipid) that precipitates. Non-exhaustive examples of hydrolytic conditions used are: acetic acid from 0.5 to 3.0% (v/v), pH 2-4, temperature 60-100° C., hydrolysis time 1-3 h. After removal of the lipid component of LPS by centrifugation, filtration or microfiltration, the solution brought to neutral pH and mixed with an equal volume of a 0.1-0.2 M NaCl solution, is again concentrated-diafiltrated.

Alternatively, acid hydrolysis (4-5% acetic acid pH<3, 1-3 h 100° C.) can be performed after deproteinization on the unconcentrated clarified broth. This experimental process also results in lipopolysaccharide hydrolysis with subsequent release of lipid A and its precipitation as well as in defructosylation of K4 polysaccharide, thereby generating chondroitin.

After hydrolysis the culture broth is cooled and centrifuged, the supernatant is adjusted to pH 7, supplemented with NaCl and then concentrated and diafiltrated to remove O-chain and residual components of the medium.

The membranes used (cassette or hollow fiber modules) are made of material compatible with the process, preferably polypropylene or polyethersulfone, and have a cut-off of 10-100 kDa, preferably 50 KDa, and a filter area of 0010-0005 m$^2$ per liter to be treated. Membrane size is limited since defructosylation involves approximately 30% difference between the molecular weight of the K4 polysaccharide and that of chondroitin, therefore the selected molecular cut of range choice allows good recovery, while maintaining the effect of purification from low molecular weight contaminants (sodium acetate, other salts, peptide residues, O-chains). Examples of operating ranges of UF process parameters are: Capacity for tangential flow recirculation 4-10 L·min$^{-1}$; trans-membrane pressure 0.8-1.4 atm; temperature 20-40° C., pH 5-8. The supernatant is concentrated up to 3-5 fold the initial volume to remove most low molecular weight contaminants (fructose, O-chains, salts) is then diafiltrated with deionized water (5.2 volumes) to complete the removal of the low molecular weight component, and push the separation of O-chains (10-15 KDa) from defructosylated chondroitin (30-50 KDa).

Recovery of Chondroitin—Chondroitin present in the retentate can be retrieved either: a) by precipitation with organic solvents (2-5 volumes of 95% ethanol v/v or acetone in the presence of 0.1-0.3M sodium chloride) and subsequent heat desiccation under vacuum; b) by lyophilization; c) by spray-drier.

The claimed downstream process enables recovery >80% of the theoretical value and leads to production of >95% pure chondroitin with an endotoxin content reduced by a factor >10$^4$, a protein content <0.05% and MW 30-50 KD.

Without intending to limit the scope of the present invention, the following examples describe the construction of recombinant over-producers of K4 polysaccharide, the fermentation strategy and the downstream process for chondroitin purification.

EXPERIMENTAL PART

Example 1

Construction of Recombinant EcK4r1

The strategy used for construction of recombinant EcK4r1 (*E. coli* K4 recombinant 1) involves the integration, into the multiple copies (1-5) of the endogenous PK4 plasmid of EcK4wt (wild type K4 *E. coli*), of an expression cassette containing the rfaH gene under control of pGapP1 (partial constitutive P1 promoter of the gene encoding glyceraldehyde-3-P dehydrogenase, GAPDH) in order to obtain constant transcription of the rfaH gene throughout the growth phase.

A) Construction of the Insertion Cassette.

1) Extraction of genomic DNA from EcK4wt—The DNeasy Blood & Tissue kit supplied by Quiagen is used for extraction of genomic DNA from EcK4wt, following the protocol provided by the manufacturer.

2) Adaptation of the integration cassette—A high fidelity DNA polymerase (Expand High Fidelity PCR System, Roche), with a reduced error rate during amplification, is used in all PCR reactions. All amplification steps are performed according to the same protocol including: 50-100 ng of starting material; primer Up to 200 mM final concentration; Primer Dw to 200 mM final concentration; 1× Taq Buffer; 1 U Taq; ultrapure milliQ H$_2$0 to a final volume of 50 μl. Table 1 lists all primers used in amplification experiments.

3) Amplification of the functional cassette (fragment I)—The cassette provided in the kit is amplified using the primer pair pK4_up and FRT_dw (Table 1). The pK4_up oligo contains a 50 bp region similar to the 5' portion of the PK4 plasmid, where the recombination event is meant to be targeted. The PCR profile used was: 94° C. for 2'; 25 cycles: 94° C. for 1', 56° C. for 1', 72° C. for 2'; 72° C. for 30".

4) Amplification of Pgap (P1) promoter (fragment II)—EcK4wt chromosomal DNA is used as template for amplification of the glyceraldehyde-3-phosphate dehydrogenase promoter. pGap_up and pGap_dw primers (Table 1) are used for the PCR reaction according to the following profile: 94° C. for 2'; 25 cycles: 94° C. for 30", 52° C. for 30", 72° C. for 30".

TABLE 1

Primers used for construction of the cassette and for screening of positive clones in EcK4r1 mutant.

| Primer | Sequence |
|---|---|
| P1 = pK4_up | 5' CAG CAC AGC AGA GCG AAG TGC ARC ATA TCC TTC CAG ATT TAA ATT CTT CAA ATT AAC CCT CAC TAA AGG GCG 3' (SEQ ID NO: 1) |
| P2 = FRT_dw: | 5' TAA TAC GAC TCA CTA TAG GGC T3' (SEQ ID NO: 2) |
| P3 = pGap_up | 5'TAA TAC GAC TCA CTA TAG GGC TC 3' (SEQ ID NO: 3) |
| P4 = pGap_dw | 5' CGG GAT CCC GAT ATT CCA CCA GCT ATT TGT TAG 3' (SEQ ID NO: 4) |
| P5 = rfaH_up | 5' CGG GAT CCC GAT GCA ATC CTG GAT TTT ACT GTA C 3' (SEQ ID NO: 5) |
| P6 = pk4_dw | 5'AAA CTG TGA TCG GGC GTA GGA ACC CGC GTA GTC ATC GTC GGC GCA GAA GTT TAG AGT TTG CGG AAC TCG GTA T 3', (SEQ ID NO: 6) |
| Control pK4_up | 5' GCC ATT AAG AAA TAC ACG ATT CC 3' (SEQ ID NO: 7) |
| Control pK4_dw | 5' ATC TTT ATT CTC ATG GCT GAA CG 3' (SEQ ID NO: 8) |

5) Amplification of the rfaH gene (fragment III)—Amplification of the rfaH gene is carried out using EcK4wt chromosomal DNA as template and primers rfaH_up and pK4_dw (Table 1). The latter contains 50 bp which are homologous to the 3' portion of plasmid PK4 where the recombination event is meant to be directed. The PCR profile used was: 94° C. for 2'; 25 cycles: 94° C. for 1', 56° C. for 1', 72° C. for 30"; 72° C. for 7'.

6) Purification and digestion of PCR products—The three products obtained from PCR reactions are separated in 1% agarose gel. Bands corresponding to the expected molecular weights are then excised and purified following the instructions of the Gel extraction kit (Quiagen). The resulting fragments are subjected to enzymatic digestion for 3 h at 37° C., respectively with XhoI for fragments I and II and with BamHI for fragments II and III (New England Biolabs) and their products are re-purified. Digestion protocol: fragment I/II/III 1000 ng; enzyme BamHI/XhoI 20 U, 1×BSA, 1× buffer, $H_2O$ to a final volume of 30 µl.

7) Ligase reactions—All reactions are carried out by setting a 3:1 ratio between the shorter fragment (Lm) and the longer fragment (LM), according to the following equation: ng LM·Kb Lm/Kb LM·3/1=ng Lm. The amount of LM DNA used to calculate the amount of Lm to be added to the reaction is 100 ng. 5 U of T4 DNA ligase are added to the reaction mix along with the specific enzyme buffer (1× final concentration). The reaction is incubated at 16° C. for 12 h.

First ligase reaction—The first ligase reaction is done with fragments I and II. The resulting product is electrophoresed in 1% agarose gel, excised and purified as described above.

Second ligase reaction—The second ligase reaction is done with the sequence obtained from the first ligase reaction (fragm. I+II) and fragment III (rfaH), reproducing the above conditions. The complete cassette (fragment I+II+III, about 2,500 bp) is purified and concentrated to 25 ng $\mu L^{-1}$.

8) Cloning in XL-Vector—The whole integration cassette is inserted in the XL cloning vector (Invitrogen), which is characterized by T-protruding ends. Taq polymerase catalyzes the addition of an extra A at the 3' end of transcripts (TA cloning). Following the protocol provided by the manufacturer, 1 µL of vector is mixed with 4 µL of PCR product and incubated at room temperature for 5 min. The sample is briefly mixed and placed in ice.

9) Transformation of E. coli TOP10 by electroporation— Electro-competent E. coli Top10 cells (Invitrogen) are transformed by electroporation to allow entry of the XL-PgaprfaH vector. A 40 µL aliquot of the cell suspension is transferred to 0.2 cm cuvettes to which the vector-insert mixture is added. The sample is incubated in ice for about 1 min and then placed in the elecroporator cell (Bio-Rad Gene Pulser), where the cells receive an electric shock (2.5 kV, 200 Ω, 25 µF). Immediately after the shock, 1 mL of SOC medium is added (composition in gr $L^{-1}$: bactotriptone 20.000, glucose 3.604, yeast extract 0.584, KCl 0.186, $MgCl_2$ 2.030, $MgSO4$ 2.465) and the cell suspension is quickly transferred to a 17×100 mm polypropylene tube which is incubated with shaking at 37° C. for 1 h. For selection of recombinant clones, aliquots of different volumes were plated on LB selective medium (composition in g $L^{-1}$, tryptone 10, NaCl 10, yeast extract 5; agar 1.5% w/v for preparation of solid medium) with kanamycin 50 µg $mL^{-1}$ at 37° C. for 12 h.

10) Screening of recombinant clones—To identify the clones containing the vector with the integration cassette, a colony PCR is performed with colonies grown after transformation. Part of the colony is resuspended in 10 µL of sterile water and incubated at 94° C. for 5 min in order to obtain cell lysis and inactivation of nucleases. Samples are then blocked in ice. M13 Fw and M13 Rw primers (Invitrogen) are used for the amplification reaction.

11) Sequencing of positive clones—Selected positive clones are subjected to extraction of plasmid DNA (QIAprep miniprep kit—Qiagen) and sequenced by the core sequencing (310 Applied Biosystems) of the University Centre of Pavia (BMR Genomics, Cribi). Vectors containing an error-free cassette are used as templates in the subsequent phases.

B) Transformation of EcK4wt Cells.

EcK4wt cells grown in LB medium for about 2 hours (OD approximately 0.4) are washed with distilled water and resuspended in 50 µL of an aqueous solution of glycerol 10% v/v. Following the instructions of the integration kit, electrocompetent cells were transformed with 800 ng of linear DNA fragment containing the complete cassette. The latter is obtained using L-pGaprfaH as template and pK4_up and rfah_dw primers. At the end of the process, bacterial isolates are obtained that contain multiple copies of the pGapRfaH construct lacking the selection marker. Table 2 shows the sequence of the pgapP1-rfaH promoter cassette.

TABLE 2

Sequence of the pgapP1-rfaH promoter cassette (SEQ ID NO: 9).

CAG CAC AGC AGA GCG AAG TGC ARC ATA TCC TTC CAG

ATT TAA ATT CTT CAA AAT TAA CCC TCA CTA AAG GGC

GGC CGC GAA GTT CCT ATT CTC TAG AAA GTA TAG GAA

CTT CCT CGA GGG CCT TTA AAA TTC GGG GCG CCG ACC

CCA TGT GGT CTC AAG CCC AAA GGA AGA GTG AGG CGA

GTC AGT CGC GTA ATG CTT AGG CAC AGG ATT GAT TTG

TABLE 2-continued

Sequence of the pgapP1-rfaH promoter cassette (SEQ ID NO: 9).

TCG CAA TGA TTG ACA CGA TTC CGC TTG ACG CTG CGT

AAG GTT TTT GTA ATT TTA CAG GCA ACC TTT TAT TCA

CTA ACA AAT AGC TGG TGG AAT ATC GGG ATC CCG ATG

CAA TCC TGG TAT TTA CTG TAC TGC AAG CGC GGG CAA

CTT CAA CGT GCC CAG GAA CAC CTC GAA AGA CAG GCT

GTG AAT TGC CTG GCA CCG ATG ATC ACC CTG GAA AAA

ATC GTG CGT GGA AAA CGT ACT GCA GTC AGT GAG CCA

TTG TTT CCC AAC TAC CTG TTT GTC GAA TTT GAT CCA

GAA GTG ATT CAT ACC ACG ACT ATC AAC GCG ACC CGC

GGT GTC AGT CAC TTC GTG CGC TTT GGC GCG TCG CCA

GCG ATA GTC CCA TCG GCG GTG ATT CAT CAG CTA TCG

GTA TAT AAA CCG AAA GAC ATT GTC GAT CCG GCA ACC

CCT TAT CCG GGA GAT AAG GTG ATT ATT ACC GAA GGC

GCG TTC GAA GGC TTT CAG GCC ATT TTC ACC GAA CCC

GAT GGT GAG GCT CGC TCC ATG CTA TTG CTT AAT CTT

ATT AAT AAA GAG ATT AAG CAC AGT GTG AAG AAT ACC

GAG TTC CGC AAA CTC TA

Example 2

Construction of Recombinant EcK4r2

The strategy used for construction of recombinant EcK4r2 (*E. coli* K4 recombinant 2) involves the integration, into the multiple copies (1-5) of the endogenous PK4 plasmid of EcK4wt, of an expression cassette containing the rfaH gene under control of pGapP1-P4 (four promoter system P1-P2-P3-P4 of the gene encoding glyceraldehyde-3-P dehydrogenase, GAPDH) in order to obtain constant transcription of the rfaH gene throughout the growth phase. The procedure is carried out as described in Example 1, except that, in this case, the construction of the cassette to be integrated in PK4 involves amplification of the whole pGapP1-P4 promoter from the EcK4wt genome. The integration site identified in PK4 is the same as in example 1. Therefore the operations for adaptation of the integration cassette are as described in Example 1, making use of the primers shown in Table 3 for amplification experiments.

TABLE 3

Primers used for cassette construction and for screening of positive clones in EcK4r3 mutant.

| Primer | Sequence |
|---|---|
| P1 = PK4_up | As in example 1, Table 2 |
| P2 = FRT_dw: | As in example 1, Table 2 |

TABLE 3-continued

Primers used for cassette construction and for screening of positive clones in EcK4r3 mutant.

| Primer | Sequence |
|---|---|
| P3 = pGaptutto_up | 5'GCC TCG AGG CGA TCA AAC AGT GAT ATA CGC 3' (SEQ ID NO: 10) |
| P4 = pGapnew_dw | As in example 1, Table 2 |
| P5 = rfaH_up | As in example 1, Table 2 |
| P6 = PK4_dw | As in example 1, Table 2 |

Example 3

Construction of Recombinant EcK4r3

The strategy used for construction of recombinant EcK4r3 (*E. coli* K4 recombinant 3) involves integration into the EcK4wt genome of an expression cassette containing the rfaH gene under pGapP1 in order to obtain constant transcription of the rfaH gene throughout the growth phase.

A) Construction of the Insertion Cassette

1) Extraction of genomic DNA from EcK4wt—Operations are as described in Example 1.

2) Adaptation of the integration cassette—Operations are as described in Example 1, using primers reported in Table 4 for amplification experiments.

3) Amplification of the functional cassette (fragment I)—The cassette provided in the kit is amplified using the primer pair Lacz_up and FRT_dw (Table 1). The LacZ_up oligo contains the 100 bp region similar to the 5' portion of the LacZ gene where the recombination event is meant to be directed. The PCR profile used was: 94° C. for 2'; 25 cycles: 94° C. for 1', 56° C. for 1', 72° C. for 2'; 72° C. for 7'.

4) Amplification of Pgap (P1) promoter (fragment II)—The procedure is as in Example 1.

5) Amplification of the rfaH gene (fragment III)—Amplification of the rfaH gene is carried out using EcK4wt chromosomal DNA as template and primers rfaH_up and LacZ_dw. The latter contains 100 bp which are homologous to the 3' portion of the segment located downstream of the LacZ gene in the EcK4wt genome, where the recombination event is meant to be directed. The PCR profile used was: 94° C. for 2'; 25 cycles: 94° C. for 1', 56° C. for 1', 72° C. for 30"; 72° C. for 7'.

TABLE 4

Primers used for cassette construction and for screening of positive clones in EcK4r3 mutant.

| Primer | Sequence |
|---|---|
| P1 = LacZ_up | 5' CAC CCT GGC GCC CAA TAC GCA AAC CGC CTC TCC CCG CGC GTT GGC CGA TTC ATT AAT GCA GCT GGC ACG ACA GGT TTC CCG ACT GGA AAG CGG GCA GTG AAA TTA ACC CTC ACT AAA GGG CGG 3' (SEQ ID NO: 11) |
| P2 = FRT_dw: | As in example 1, Table 2 |
| P3 = pGap_up | As in example 1, Table 2 |

TABLE 4-continued

Primers used for cassette construction and for screening of positive clones in EcK4r3 mutant.

| Primer | Sequence |
|---|---|
| P4 = pGap_dw | As in example 1, Table 2 |
| P5 = rfaH_up | As in example 1, Table 2 |
| P6 = LacZ_dw | 5'AAA AGA ATA AAC CGA ACA TCC AAA AGT TTG TGT TTT TTA AAT AGT ACA TAA TGG ATT TCC TTA CGC GAA ATA CGG GCA GAC ATG GCC TGC CCG GTT ATT TAG AGT TTG CGG AAC TCG GTA TTC 3' (SEQ ID NO: 12) |

6) Purification and digestion of PCR products—The procedure is as in Example 1.
7) Ligase reactions—The procedure is as in Example 1.
8) Cloning in XL-Vector—The procedure is as in Example 1.
9) Transformation of *E. coli* TOP10 by electroporation—The procedure is as in Example 1.
10) Screening of recombinant clones—The procedure is as in Example 1.
11) Sequencing of positive clones—The procedure is as in Example 1.

B) Transformation of EcK4wt Cells.

The procedure is as in Example 1 with the only difference that the complete cassette contained in the linear DNA fragment is obtained using XL-pGaprfaH as template and primers LacZ_Up e LacZ_Dw. Table 5 shows the sequence of the pgapP1-rfaH promoter cassette.

TABLE 5

Sequence of the pgapP1-rfaH promoter cassette (SEQ ID NO: 13).

CAC CCT GGC GCC CAA TAC GCA AAC CGC CTC TCC CCG

CGC GTT GGC CGA TTC ATT AAT GCA GCT GGC ACG ACA

GGT TTC CCG ACT GGA AAG CGG GCA GTG AAA TTA ACC

CTC ACT AAA GGG CGG CCG CGA AGT TCC TAT TCT CTA

GAA AGT ATA GGA ACT TCC TCG AGG GCC TTT AAA ATT

CGG GGC GCC GAC CCC ATG TGG TCT CAA GCC CAA GGG

AAG AGT GAG GCG AGT CAG TCG CGT AAT GCT TAG GCA

CAG GAT TGA TTT GTC GCA ATG ATT GAC ACG ATT CCG

CTT GAC GCT GCG TAA GGT TTT TGT AAT TTT ACA GGC

AAC CTT TTA TTC ACT AAC AAA TAG CTG GTG GAA TAT

CGG GAT CCC GAT GCA ATC CTG GTA TTT ACT GTA CTG

CAA GCG CGG GCA ACT TCA ACG TGC CCA GGA ACA CCT

CGA AAG ACA GGC TGT GAA TTG CCT GGC ACC GAT GAT

CAC CCT GGA AAA AAT CGT GCG TGG AAA ACG TAC TGC

AGT CAG TGA GCC ATT GTT TCC AAC TAC CT GTT TGT

CGA ATT TGA TCC AGA AGT GAT TCA TAC CAC GAC TAT

CAA CGC GAC CCG CGG TGT CAG TCA CTT CGT GCG CTT

TABLE 5-continued

Sequence of the pgapP1-rfaH promoter cassette (SEQ ID NO: 13).

TGG CGC GTC GCC AGC GAT AGT CCC ATC GGC GGT GAT

TCA TCA GCT ATC GGT ATA TAA ACC GAA AGA CAT TGT

CGA TCC GGC AAC CCC TTA TCC GGG AGA TAA GGT GAT

TAT TAC CGA AGG CGC GTT CGA AGG CTT TCA GGC CAT

TTT CAC CGA ACC CGA TGG TGA GGC TCG CTC CAT GCT

ATT GCT TAA TCT TAT TAA TAA AGA GAT TAA GCA CAG

TGT GAA GAA TAC CGA GTT CCG CAA ACT CTA TAA TAA

CCG GGC AGG CCA TGT CTG CCC GTA TTT CGC GTA AGG

AAA TCC ATT ATG TAC TAT TTA AAA AAC ACA AAC TTT

TGG ATG TTC GGT TTA TTC TTT T

Example 4

Construction of Recombinant EcK4r4

The strategy used for construction of the recombinant EcK4r4 (K4 recombinant *E. coli* 4) involves engineering EcK4wt by use of insertional mutagenesis based on the use of transposable elements. To this end, the characteristics of the *E. coli* gene cluster have been exploited, namely the presence of the IS2 insertion sequence and the experimental evidence that rfaH overexpression can influence production of the K4 polysaccharide.

TABLE 6

Primer for construction of the IS2-rfaH cassette.

| Primer | Sequence |
|---|---|
| rfaHIS2_Up | 5'- CGG GAT CCG AAT GCA ATC CTG GTA TTT ACT G -3' (SEQ ID NO: 14) |
| rfaHIS2_Dw | 5' - CGG AGC TCT TAG AGT TTG CGG AAC TCG GT - 3' (SEQ ID NO: 15) |
| RIR | 5' - TGG ATT TGC CCC TAT GTT TCC AGA TAC CTG TTA TCA CTT AAA GCT - 3' (SEQ ID NO: 16) |
| ANTIRIR | 5' - TTA AGT GAT AAC AGG TAT CTG GAA ACA TAG GGG CAA ATC CA - 3' (SEQ ID NO: 17) |
| IRL_Up | 5'-TAG ACT GGC CCC CTG AAT CTC C-3' (SEQ ID NO: 18) |
| IRL_Dw | 5'- CGG GAT CCT CCA ATG ACT AGT CTA AAA ACT AG-3' (SEQ ID NO: 19) |

Generally the IS2 sequence contains a promoter followed by a gene encoding a transposase, these genes have flanking sequences termed IRL (LIR) and RIR. The strategy is based on construction of a modified IS2 element containing the rfaH gene in place of the transposase encoding gene. IRL, RIR and rfaH were amplified from *E. coli* K4 genomic DNA, using primers reported in Table 6, and subsequently digested with appropriate restriction enzymes to create fragments with compatible ends and ready to be subjected to a ligation reaction. The resulting fragment (IRL-rfaH-RIR) was amplified and inserted into the XL cloning vector (Invitrogen) that was subsequently used to transform E. coli K4 cells. A random integration event/events took place independently (after the evolution cycles for expulsion of the vector and establishment of a stable mutant, e.g. 3 consecutive growth cycles in flask during 24 h) yielding a mutant with at least one copy of the rfaH gene overproducing the K4 polysaccharide.

TABLE 7

IS2-rfaH sequence (SEQ ID NO: 20)

```
TAG ACT GGC CCC CTG AAT CTC CAG ACA ACC AAT ATC
ACT TAA ATA AGT GAT AGT CTT AAT ACT AGT TTT TAG
ACT AGT CAT TGG AGG ATC CGA ATG CAA TCC TGG TAT
TTA CTG TAC TGC AAG CGC GGG CAA CTT CAA CGT GCC
CAG GAA CAC CTC GAA AGA CAG GCT GTG AAT TGC CTG
GCA CCG ATG ATC ACC CTG GAA AAA ATC GTG CGT GGA
AAA CGT ACT GCA GTC AGT GAG CCA TTG TTT CCC AAC
TAC CTG TTT GTC GAA TTT GAT CCA GAA GTG ATT CAT
ACC ACG ACT ATC AAC GCG ACC CGC GGT GTC AGT CAC
TTC GTG CGC TTT GGC GCG TCG CCA GCG ATA GTC CCA
TCG GCG GTG ATT CAT CAG CTA TCG GTA TAT AAA CCG
AAA GAC ATT GTC GAT CCG GCA ACC CCT TAT CCG GGA
GAT AAG GTG ATT ATT ACC GAA GGC GCG TTC GAA GGC
TTT CAG GCC ATT TTC ACC GAA CCC GAT GGT GAG GCT
CGC TCC ATG CTA TTG CTT AAT CTT ATT AAT AAA GAG
ATT AAG CAC AGT GTG AAG AAT ACC GAG TTC CGC AAA
CTC TAA GAG CTC TTA AGT GAT AAC AGG TAT CTG GAA
ACA TAG GGG CAA ATC CA.
```

Example 5

Production in Flask of the K4 Capsular Polysaccharide Using EcK4r1, EcK4r2 and EcK4r3 Mutants and the Wild Type EcK4wt Strain To assess comparatively the production efficiency of the K4 capsular polysaccharide, the mutant strains EcK4r1, EcK4r2 and EcK4r3 and the wild type strain EcK4wt are grown in flask, varying the nutrient sources: medium 1, glycerol 10 g·L$^{-1}$+soy 1 g·L$^{-1}$; medium 2, glycerol 10 g·L$^{-1}$+casamino acids 2 g·L$^{-1}$; medium 3, glucose 10 g·L$^{-1}$+yeast extract 1 g·L$^{-1}$; medium 4, glucose 10 g·L$^{-1}$+yeast extract 2 g·L$^{-1}$. All media have a pH of 7.5 and contain the same salt solution: K2HPO$_4$ 10 g·L$^{-1}$; KH$_2$PO$_4$ 2 g·L$^{-1}$; MgCl$_2$ 0.1 g·L$^{-1}$; sodium citrate 0.5 g·L$^{-1}$ (NH$_4$)$_2$SO$_4$ 1 g·L$^{-1}$.

The flasks are incubated in an orbital shaker operating at 200 rpm. At an absorbance value of approximately 5.0 OD$_{600}$ (12-16 hours incubation) recombinant strains have an average production of K4 capsular polysaccharide which is 1.8 to 3.0 fold higher than the wild type strain (Table 8). The genetic stability of recombinants is evaluated by successive growth cycles carried out in flask, which confirm that the observed productivity levels are maintained. PCR analyses performed after each growth cycle show that the constructs are still present in the genetic material of recombinants after 10 days of culture.

TABLE 8

Production of K4 capsular polysaccharide in flask using different culture media.

| | Medium | | | |
|---|---|---|---|---|
| | 1 | 2 | 3 | 4 |
| strain | K4 polysaccharide (mgL$^{-1}$) | | | |
| EcK4wt | 95 ± 10 | 80 ± 10 | 90 ± 10 | 100 ± 15 |
| EcK4r1 | 170 ± 18 | 150 ± 20 | 165 ± 15 | 180 ± 18 |
| EcK4r2 | 280 ± 20 | 250 ± 20 | 270 ± 25 | 300 ± 25 |
| EcK4r3 | 210 ± 20 | 190 ± 15 | 200 ± 15 | 230 ± 20 |
| EcK4r4 | 190 ± 20 | 180 ± 15 | 200 ± 15 | 210 ± 30 |

Example 6

Production of K4 Capsular Polysaccharide by Batch Fermentation, Using EcK4r1, EcK4r2 and EcK4r3 Mutants and the Wild Type EcK4wt Strain Growth of EcK4r1, EcK4r2 and EcK4r3 mutant strains and of the wild type EcK4wt strain is carried out in a 2.5 L bioreactor (Biostat C Plus of B. Biotech International, Melsungen, Germany) equipped with a digital control unit (DCU) for continuous measurement of the fermentation parameters (pH, pO$_2$, agitation speed, aeration, temperature). Growth is carried out using culture media 1 and 4 reported in Table 8 of Example 5. Registration and control of fermentation parameters are managed through the Multi Fermentor Control System data acquisition program for Windows NT (MFCS/win software B. Braun Biotech International). A variable volume of the culture from flask is used as inoculum, that is calculated to give a starting OD$_{600}$ between 0.08 and 0.10. The fermentation conditions used were: temperature 37° C.; pH 7.5 controlled by NH$_4$OH (50% v/v) or H$_2$SO$_4$ (30% v/v) addition; initial concentration of glycerol 10 g·L$^{-1}$; initial agitation value 500 rpm; initial air flow value 2-3 Lmin$^{-1}$ (agitation and aeration are automatically adjusted during fermentation to ensure that the pO$_2$ is higher than 20% at any time. Growth course is monitored by measuring the absorbance at 600 nm, the kinetics of glycerol consumption, the formation of organic acids and the production of K4 capsular polysaccharide. Growth is generally interrupted at the beginning of the stationary phase of growth after 20-24 h from the start of fermentation. As reported in Table 9, the productivity recombinant strains in the best medium is 1.3 to 1.8 fold higher than the wild type strain.

TABLE 9

Production of K4 capsular polysaccharide by batch fermentation in different culture media.

| | Medium | |
|---|---|---|
| | 1 | 4 |
| strain | K4 polysaccharide (mgL$^{-1}$) | |
| EcK4wt | 300 ± 20 | 310 ± 25 |
| EcK4r1 | 420 ± 30 | 470 ± 40 |
| EcK4r2 | 450 ± 25 | 490 ± 35 |
| EcK4r3 | 475 ± 35 | 525 ± 25 |
| EcK4r4 | 445 ± 25 | 480 ± 25 |

Example 7

Production of K4 Capsular Polysaccharide by Fed-Batch Fermentation, Using EcK4r1, EcK4r2 and EcK4r3 Mutants and the Wild Type EcK4wt Strain The procedure is as described for batch fermentations in Example 5, using the same culture media, except that after 5-7 hours, when $pO_2$ and pH values increase, the fed phase is started and carried out for an average of 25 hours. The addition of nutrients is maintained below the rate of substrate uptake to avoid the phenomenon of overflow metabolism. This is achieved in a metabolically controlled manner by adjusting the addition of nutrients according to the $pO_2$ of the medium, which must be maintained at about 30%. In fact, the DOT (Dissolved Oxygen Tension) increases rapidly when all the substrate in the fermentor is consumed, but addition of the carbon source to the reactor results in a decrease of the DOT. In practice, controlled addition of a concentrated solution of nutrients is realized by means of a PID controller connected to a feeding pump supplying the nutrients. When the lack of nutrients results in an increase of DOT, feeding is automatically activated until reaching the $pO_2$ set point. At this point the feeding pump is blocked until the carbon source is consumed, resulting in a sudden new increase of the $pO_2$ value and triggering a new feeding round. The concentrated nutrient solutions used are: medium 1 glycerol 4000 $g \cdot L^{-1}$+soy flour 40 $g \cdot L^{-1}$ w/v; medium 2 glucose 400 $g \cdot L^{-1}$+yeast extract 80 $g \cdot L^{-1}$. At the end of the process the recombinant strains use: For medium 1, about 60 $g \cdot L^{-1}$ of glycerol and 5.8 $g \cdot L^{-1}$ of soy with a production of K4 capsular polysaccharide which is 1.4-1.8 fold higher than that of wild type (Table 10) but consumes 38% more nutrients; for medium 4, 68 $g \cdot L^{-1}$ of glucose and 13.6 $g \cdot L^{-1}$ YE, with a production of K4 capsular polysaccharide which is 1.5-1.9 fold higher than that of wild type (Table 9) but consumes 40% more nutrients.

TABLE 10

Production of K4 capsular polysaccharide by fed-batch fermentation in different culture media.

| | Medium | |
|---|---|---|
| | 1 | 4 |
| strain | K4 polysaccharide (mg $L^{-1}$) | |
| EcK4wt | 1.400 ± 150 | 1500 ± 200 |
| EcK4r1 | 2.000 ± 100 | 2.350 ± 150 |
| EcK4r2 | 2.150 ± 130 | 2.500 ± 230 |
| EcK4r3 | 4.000 ± 100 | 5.100 ± 250 |
| EcK4r3 | 3.000 ± 100 | 3.500 ± 250 |

Example 8

Production of K4 Capsular Polysaccharide by Fermentation in Microfiltration Regimen, Using EcK4r1, EcK4r2 and EcK4r3 Mutants and the Wild Type EcK4wt Strain The procedure is as described for fermentations in Example 6, using the same culture media except that, after an initial batch phase (7 h) and a subsequent fed-batch phase (5 h), microfiltration modules are activated for replacement of the depleted medium. The microfiltration phase lasts an average of 35 h. In this case the microfiltration process is carried out using a hollow fiber module made of polyethersulfone with cut-off of 0.22 μm, and an area comprised between 0.02 and 0.1 $m^2$. Examples of operating ranges of MF process parameters are: Capacity for tangential flow recirculation 6-10 $Lmin^{-1}$; trans-membrane pressure 0.8-1.2 atm; room temperature. The exchange of 1 volume of culture in approximately 2-4 h was obtained under these conditions.

In both feed and microfiltration phases, the rate of nutrient addition is controlled so as to maintain the $pO_2$ of the culture medium at about 30%, using a PID controller connected to the feeding pump supplying the nutrients. When the lack of nutrients results in an increase of DOT, feeding is automatically activated until reaching the $pO_2$ set point. At this point the feeding pump stabilizes at a minimum value of rounds/minute in order to ensure, unlike fed-batch experiments, the maintenance of a minimum concentration of carbon in the fermentation vessel, despite the continuous supply of medium. The depletion of the carbon source determines again a sudden rise of the $pO_2$ value, triggering a new feeding round at a rotation speed of the peristaltic pump which is higher than the minimum that was set by default. During microfiltration, the volume of bacterial culture is kept constant by a special control loop (level controller) by addition of a mineral salt solution which is identical to that used in the growth medium. Using the same saline solution, backflushing is performed every hour to decrease the fouling effects during microfiltration.

During the experiments, agitation and ventilation were varied from 250 to 1.000 rpm and from 1 to 1.6 $Lmin^{-1}$, respectively, to maintain the percentage of dissolved oxygen close to 20% saturation.

At the end of the process, recombinant strains use: for medium 1, about 130 $gL^{-1}$ of glycerol and 13 $gL^{-1}$ of soy with a production of K4 capsular polysaccharide which is 2.2-2.6 fold higher than that of wild type (Table 10) but consumes 30% more nutrients; for medium 4, about 90-100 $g \cdot L^{-1}$ of glucose and 18-20 $g \cdot L^{-1}$ YE, with a production of K4 capsular polysaccharide which is 2.3-2.7 fold higher than that of wild type (Table 11) but consumes 25% more nutrients. In both cases the volume of microfiltrate is about 10-12 L and the amount of K4 capsular polysaccharide found in the microfiltrate is 25-30% of the total product.

TABLE 11

Production of K4 capsular polysaccharide by fermentation in microfiltration regimen in different culture media.

| | Medium | |
|---|---|---|
| | 1 | 4 |
| strain | K4 polysaccharide (mg$L^{-1}$) | |
| EcK4wt | 3.500 ± 100 | 3.750 ± 150 |
| EcK4r1 | 7.800 ± 185 | 8.600 ± 160 |
| EcK4r2 | 8.200 ± 150 | 8.900 ± 180 |
| EcK4r3 | 8.400 ± 190 | 9.200 ± 150 |

Example 9

Production of K4 Capsular Polysaccharide on a 1 $m^3$ Scale

The recombinant strain EcK4r3 is employed using culture medium 1 from Example 4. The fermentation product (40-60 L) obtained from a batch process as described in Example 5, and using a 75 L fermentor, is used as inoculum. The inoculum is incubated in the fermentor for 6-8 h until a cell density of 5±1 $OD_{600}$ is reached. The $m^3$ production scale employs a 1.2 $m^3$ fermentor containing 1 $m^3$ of culture medium. Fermentation is carried out by the same strategy described in Example 7, except that an external microfiltration unit is used that consists of a hollow fiber module with a 8-10 m² filter area operating at a tangential flow of 10 Lmin⁻¹. The duration of batch and fed-batch phases is 5-7 h and 4-6 h, respectively. In the fed-batch phase, 40 L of concentrated solution of nutrients are added overall, for a total of 12.5 kg of glucose and 2.5 kg of yeast extract. The phase in microfiltration regimen lasts 24-36 h and the volume of the microfiltrate is 6-7 m³.

Overall, 9 Kg of K4 capsular polysaccharide are obtained, 30% of which is found in the microfiltrate.

Example 10

Obtaining Chondroitin by Process 1

The example describes the downstream processing of a fermentation broth obtained as described in Example 9. At the end of fermentation, the cellular component is removed from the culture broth (1000 L) by continuous centrifugation using an alpha-laval centrifuge (Clara80) operating at 6000 rpm at 15-25° C. The microfiltrate from the last phase of fermentation (7000 L) is added to the clear supernatant, followed by addition of a protease (flavourzyme) from *Aspergillus oryzae* (10 µLL⁻¹, 500 Ug⁻¹, 2-5 UL⁻¹ final) and incubation with stirring for 2 h at room temperature or at 4° C. for 12-16 h to hydrolyze proteins. The solution is subsequently ultrafiltered on a micro/ultra/diafiltration tangential Millipore system mounted on a special skid with a reservoir capacity of 1 m³, equipped with hollow fiber modules or cassettes (100 kDa cutoff, filter area 40 m²). When the volume is reduced to 90-100 L, diafiltration is carried out with ultrapure water (HPW) at a constant volume, until a residual conductivity below 500 µSi·cm (5 volumes) is obtained. 1% v/v acetic acid is then added and the solution is heated at 100° C. for 1.25 h. Defructosylation of the K4 capsular polysaccharide and hydrolysis of LPS are simultaneously obtained under these conditions, thus separating the oligosaccharide component (o-chain) from the lipid component (lipid A) which precipitates. The suspension is clarified by continuous centrifugation at 6.000 rpm (1 h) or by sedimentation at 4° C. (16-18 h). The clear solution (70-80 L), adjusted to pH 7 by addition of NaOH and supplemented with NaCl to 0.2M concentration, is subjected to ultrafiltration-diafiltration using the same Millipore apparatus equipped with cassettes/hollow fiber modules (10 m²) made of polyethersulfone or polypropylene with a cutoff of 30-100 KDa. The solution is initially concentrated (2-5×) and then diafiltrated until conductivity is less than 80-100 µSicm⁻¹. The solution is then esiccated by lyophilisation. The overall yield of the purification process is 75%. 4,790 g of chondroitin sodium salt are obtained with the following specifications: white powder, 12% residual H₂O content, purity >95%, MW 38±2 kDa.

Example 11

Obtaining Chondroitin by Process 2

The example describes the downstream processing of a fermentation broth obtained as described in Example 8. At the end of fermentation the cellular component is removed from the culture broth (1,000 L) by continuous centrifugation using an alpha-laval centrifuge (Clara80) operating at 6000 rpm at 15-25° C. The microfiltrate from the last phase of fermentation (7000 L) is added to the clear supernatant, followed by addition of 4% v/v acetic acid until a pH between 2.8 and 3.0, heating the solution at 100° C. for 1 h. These conditions result in defructosylation of the K4 capsular polysaccharide and splitting of lipid A from LPS which precipitates as a waxy solid. The latter is separated by sedimentation at 4° C. (10-16 h), followed by continuous centrifugation at 6,000 rpm (approx. 2 hours) or by sedimentation. The clear solution (approximately 7.500 L), adjusted to pH 7 by addition of NaOH and supplemented with NaCl to 0.1 M concentration, is subjected to ultrafiltration-diafiltration using the above described apparatus equipped with cassettes/hollow fiber modules (10 m²) made of polyethersulfone with a cutoff of 50 KDa. The solution is concentrated (40×) and diafiltrated until conductivity is below 80-100 µSicm⁻¹. The solution, about 200 L, is supplemented with NaCl to 0.1 M final concentration and then with 2 volumes of 95% ethanol for precipitation of sodium chondroitin. The wet precipitate collected after sedimentation (approximately 6,500 g) is then washed with anhydrous ethanol (15 L) and desiccated under vacuum at 30° C. The overall yield of the purification process is 85%. 5,430 g of chondroitin sodium salt are obtained with the following specifications: white powder, 12% residual H₂O content, purity >94%, MW 35±2 kDa.

Example 12

Obtaining Chondroitin by Process 3

The example describes the downstream processing of a fermentation broth obtained as described in Example 8, using only membrane processes. At the end of fermentation, the cellular component is removed from the culture broth present in the fermentor (1.000 L) extending the microfiltration phase without the addition of saline. After concentrating the broth to 300 L, one volume of ultrapure water is added and concentration by microfiltration is again performed to 300 L to increase recovery of the capsular polysaccharide; this washing step is repeated 2 times. After addition of the microfiltrate obtained during fermentation (6.000 L), the fermentation broth devoid of cells (approximately 1200 L) is treated as described in Example 9, first with protease, then by hydrolysis with acetic acid and finally ultrafiltrated-diafiltrated. The so obtained concentrate is esiccated by a spray-drier The overall yield of the purification process is 90%. 5,750 g of chondroitin sodium salt are obtained with the following specifications: white powder, 10% residual H₂O content, purity >93%, MW 38±2 kDa.

Example 13

Obtaining Chondroitin by Process 4

The example describes the downstream processing of a fermentation broth obtained as described in Example 8. At the end of fermentation, the culture broth (1.000 L) is supplemented with trichloroacetic acid (TCA 50% v/v) to 5% of the volume, until pH<4. This broth is then filtered on diatomaceous earth or celite with the aid of a FUNDA type plate filter. The clarified broth is microfiltered with the aid of an asymmetric capsular device (0.2-0.6 m; GE) in dead-end mode and neutralized by addition of NaOH. About 7.000 L of microfiltrate are added to this material, and the clarified broth is subsequently concentrated by ultrafiltration and diafiltration; when the volume is reduced to 200 L, diafiltration with ultrapure water (HPW) at constant volume is performed until residual conductivity below 500 µSicm⁻¹ (5 volumes) is obtained. 1% v/v acetic acid is then added and the solution is heated at 100° C. for 1.25 h. After centrifugation, the clear supernatant (160 L), adjusted to pH 7 by addition of NaOH and supplemented with NaCl until 0.2M concentration, is subjected to ultrafiltration-diafiltration using the same Millipore apparatus equipped with cassettes/hollow fiber modules (10 m$^2$) made of polyethersulfone or polypropylene with a cutoff of 50 KDa. The solution is initially concentrated (3×) and then diafiltrated until the conductivity is below 100 μSicm$^{-1}$. Subsequently, the solution brought to 0.125M NaCl is supplemented with 2 volumes of acetone to precipitate the chondroitin. The precipitate, collected on filters or sedimented, is dried in an oven at 40° C. The overall yield of the purification process is 70%. 4,480 g of chondroitin are obtained with the following specifications: white powder, 12% residual H$_2$O content, purity >92%, MW 35±2 kDa.

The invention claimed is:

1. A process for the preparation of chondroitin from a bacterial capsular polysaccharidic precursor comprising
growing and amplifying a bacterium transformed with multiple copies of an expression cassette comprising a nucleotide sequence encoding an rfaH protein, said rfaH protein-coding sequence comprising the nucleotide sequence of SEQ ID NO: 9, SEQ ID NO: 13 or SEQ ID NO: 20, wherein said bacterium is *Escherichia coli*, selected from strains: K5, K4, and K30 having as polysaccharide precursor a K5, K4 and K30 capsular polysaccharide, respectively, or said bacterium is *Pasteurella multocida*; and wherein said growing and amplifying step comprises a first batch phase, a second fed-batch phase and a microfiltration regimen;
recovering a cell-free concentrated supernatant via ultra-filtration;
hydrolyzing the cell-free concentrated solution; and
recovering said chondroitin from said cell-free concentrated solution.

2. The process according to claim 1, wherein the bacterium is *Escherichia coli* strain K4 having as capsular polysaccharide chondroitin fructosylated on position 3 of glucuronic acid residues.

3. The process according to claim 2, wherein the *E. coli* K4 strain is selected from the group consisting of: strain having deposit number ATCC 23502 (American Type Culture Collection—USA), strain Bi 8337/41 (International *Escherichia* Centre—Denmark), strain NCTC 9005 (National Collection of Type Cultures—UK) and strain U1-41 2616 (Freiburg Collection).

4. The process according to claim 1, wherein said expression cassette comprises chromosomal DNA, plasmid elements or transposable elements.

5. The process according to claim 4, wherein said plasmid element comprises the nucleotide sequences of SEQ ID NO: 1 and SEQ ID NO: 6.

6. The process according to claim 1, wherein the expression cassette comprises a constitutive promoter.

7. The process according to claim 1, wherein bacterial growth and amplification are carried out during said batch phase and wherein, at the end of the batch phase, as nutrients decrease, fermentation is carried on in the fed-batch phase by addition of a nutrient solution.

8. The process according to claim 7, wherein:
a) the batch phase is carried out for a time ranging from 6 to 8 hours and biomass concentration expressed as wet weight ranges from 0.6 to 1%;
b) the fed batch phase is initiated after 7-8 h of fermentation and is carried out for a time ranging from 6 to 12 hours and biomass concentration expressed as wet weight ranges from 15 to 40gL$^{-1}$;

wherein the fed batch phase b) is integrated with microfiltration and wherein fermentation volume is kept constant by addition of saline with a composition compatible with that used in the fermentation broth.

9. The process according to claim 8, wherein the microfiltration is carried out with flat configuration membranes or hollow fiber membranes, with a cut-off between 0.1 and 0.5 µm, said membranes operating with a tangential flow of 80-120 L(min·m$^2$)$^{-1}$.

10. The process according to claim 9, wherein the cut-off is between 0.1 and 0.2 µm said membranes operating with a tangential flow of 90-100 L(min·m$^2$)$^{-1}$.

11. The process according to claim 1, further comprising chemically sulfating the recovered chondroitin.

* * * * *